United States Patent [19]

Heimburger et al.

[11] Patent Number: 5,091,363
[45] Date of Patent: Feb. 25, 1992

[54] AGENT FOR THE THERAPY OF FACTOR VIII-RESISTANT HEMOPHILIA A, AND A PROCESS FOR THE PREPARATION THEREOF

[75] Inventors: Norbert Heimburger, Marburg; Karlheinz Wenz, Weimar; Wilfried Wormsbächer, Kirchhain, all of Fed. Rep. of Germany

[73] Assignee: Behringwerke Aktiengesellschaft, Marburg/Lahn, Fed. Rep. of Germany

[21] Appl. No.: 230,717

[22] Filed: Aug. 10, 1988

Related U.S. Application Data

[63] Continuation of Ser. No. 76,600, Jul. 22, 1987, abandoned.

[30] Foreign Application Priority Data

Jul. 24, 1986 [DE] Fed. Rep. of Germany ....... 3625090

[51] Int. Cl.$^5$ ............................................. A61K 37/02
[52] U.S. Cl. ........................................ 514/2; 424/94.3; 424/529; 514/8; 514/21; 530/381; 530/383; 530/830
[58] Field of Search ............... 530/380, 382, 383, 395, 530/381, 830; 514/21, 2, 8; 424/101, 94.3

[56] References Cited

U.S. PATENT DOCUMENTS

| | | | |
|---|---|---|---|
| 4,160,025 | 7/1979 | Eibl et al. | 424/101 |
| 4,297,344 | 10/1981 | Schwinn et al. | 424/101 |
| 4,340,589 | 7/1982 | Uemura et al. | 424/101 |
| 4,404,132 | 9/1983 | Mitra | 424/101 |
| 4,446,134 | 5/1984 | Naito et al. | 424/101 |
| 4,465,623 | 8/1984 | Chanas et al. | 530/415 |
| 4,522,751 | 6/1985 | Linnau et al. | 424/101 |
| 4,610,880 | 9/1986 | Giles et al. | 424/101 |
| 4,650,858 | 3/1987 | Rasmussen et al. | 424/101 |
| 4,710,381 | 12/1987 | Kunicki et al. | 424/101 |

FOREIGN PATENT DOCUMENTS

| | | | |
|---|---|---|---|
| 3237512 | 4/1984 | Fed. Rep. of Germany | 424/101 |
| 0127308 | 10/1981 | Japan | 424/101 |
| 8002426 | 11/1980 | PCT Int'l Appl. | 424/101 |
| 2085729 | 10/1980 | United Kingdom | 424/101 |

OTHER PUBLICATIONS

Bajaj et al., J. Biol. Chem., 260(12), 11574–80, (1985).
Barrowcliffe et al., J. Lab. Clin., 101(1):34, 1983.
Elodi et al., Chem. Abs. 91:190435v, 1979 (Thromb Res, 15, 617–29, 1979).
Veradi et al. Chem. Abs. 94:78702r, 1981 (Thromb Res. 19, 571–8, 1980).
Van Dieijan et al., Chem. Abs. 94:171881h, 1981 (JBC, 256(7), pp. 3433–3442, 1981).
Barrowcliffe et al. Chem. Abs. 101:88685q, 1984 (Prog. Clin. Biol. Res., 251–03, 150, 1984).
Preston et al., Chem. Abs. 88:83671k, 1978.

*Primary Examiner*—Sam Rosen
*Attorney, Agent, or Firm*—Finnegan, Henderson, Farabow, Garrett, and Dunner

[57] ABSTRACT

An agent for the therapy of hemophilia A which is resistant to treatment with factor VIII is described, and is obtainable by maintaining a mixture of factor VIII, antithrombin III, a phospholipid and calcium ions in an aqueous solution at a temperature of from 1° to 45° C. for at least one minute, adding factor IX, and maintaining the solution at a temperature of from 1° to 45° C. until addition of a sample of this solution to an inhibitor plasma results in a partial thromboplastin time (PTT) of 15 to 30 seconds, where appropriate adding a polyol and, where appropriate, an amino acid, and, where appropriate, drying the solution.

6 Claims, 1 Drawing Sheet

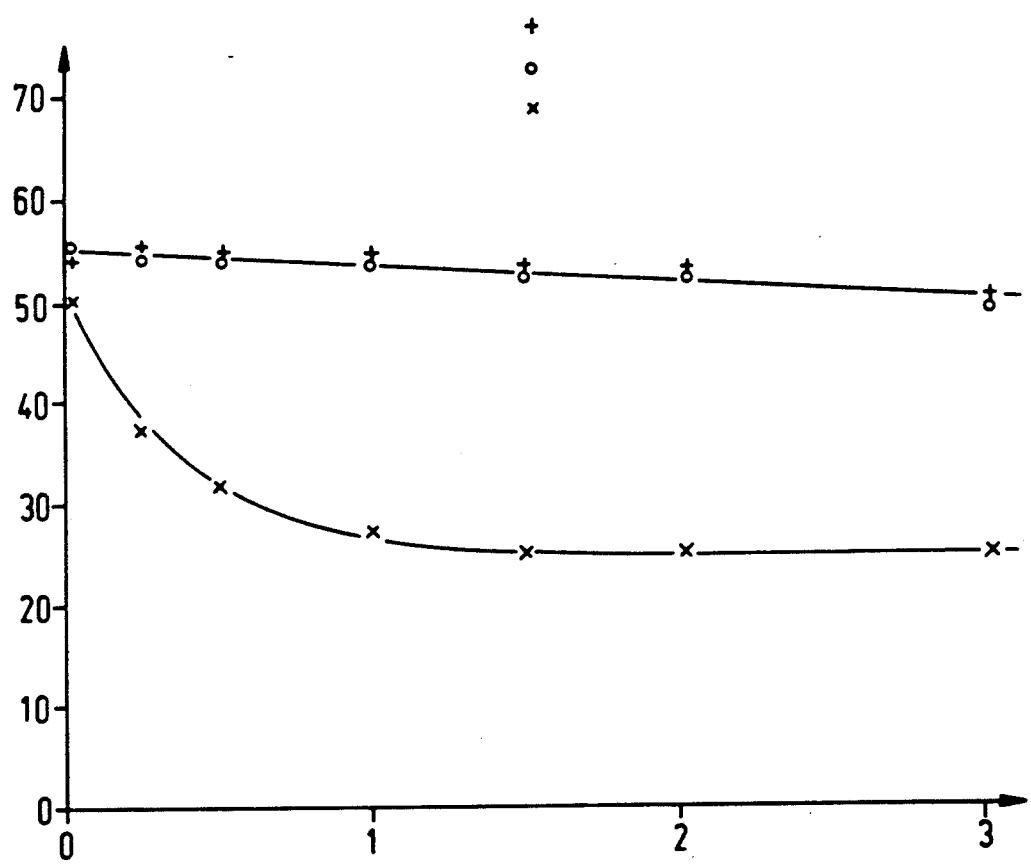

AGENT FOR THE THERAPY OF FACTOR VIII-RESISTANT HEMOPHILIA A, AND A PROCESS FOR THE PREPARATION THEREOF

This application is a continuation of application Ser. No. 076,600, filed July 22, 1987, now abandoned.

The invention relates to an agent for the treatment of patients who have hemophilia A and do not respond to the conventional treatment with factor VIII, and to a process for the preparation thereof.

Up to about one quarter of patients who have hemophilia A and are treated with factor VIII concentrates develop what are called inhibitor hemophilias. It is characteristic of these that non-precipitating isoantibodies against the subunit of the factor VIII molecule which harbors the clotting activity (F VIII:C) circulate in the blood of the patient. These antibodies, which are found in titers which may reach very high levels, namely from 100 up to a few 1000 U/ml, in the plasma of hemophiliacs, neutralize corresponding activities of F VIII when they are infused for replacement in patients who do not synthesize factor VIII or synthesize it in inadequate amounts. The amount of inhibiting antibodies is often so high that even administration of large amounts of factor VIII do not result in successful therapy.

A number of measures have been tried for the treatment of the serious hemorrhages which often occur in patients who have hemophilia A and have developed antibodies, but these measures have been only partially successful. These measures include infusion of prothrombin complex concentrates (PCC) which contain factors II, VII, IX and X. In emergency situations there has even been use of factor VIII from animal plasma, predominantly from bovine or porcine plasma, with acceptance of the risk of administration of foreign protein. In recent times, activated coagulation factors have also been used with a certain success.

Agents of this type contain activated coagulation enzymes whose effect is difficult to control, so that it is impossible to rule out the risk of thrombosis.

There have also been attempts to remove these antibodies from the patient's plasma using the principle of immuno-adsorption onto factor VIII which has been rendered insoluble. In addition, plasmapheresis is also used for eliminating the antibodies. Finally, therapeutic inhibition of the formation of antibodies against F VIII:C is also attempted.

In recent times, complexes of F VIII with phospholipids have also been considered for the therapy of inhibitor hemophilias (J. Lab. Clin. Med. 101, 34–43, 1983). This approach is based on the recognition that F VIII binds phospholipids, and these binding sites are exactly the ones against which the isoantibodies of the hemophilia patients are directed. Consistent with this, F VIII phospholipid complexes are protected from attack by inhibitors of the iso- and auto-antibody type. Corresponding complexes, as well as activated enzymes, have also been suggested as the active principle of FEIBA (factor VIII inhibitor bypass activity) (Thrombosis Research 21, 181–186, 1981).

There are good experimental foundations for the efficacy of F VIII-phospholipid complexes. Thus, for example, it is demonstrated in J. Lab. Clin. Med. 101, 34–43 (1983) that when a complex of this type is added together with F IXa to an inhibitor plasma it initiates the formation of thrombin, and thus also coagulation, as soon as calcium ions are added. Although this therapeutic concept appears promising, nevertheless it has the disadvantage that activated factors can be manipulated only with difficulty in the production process and, moreover, it is impossible to estimate their in vivo effect.

All these methods have disadvantages.

Accordingly, the present invention has the object of making available an agent for the treatment of factor VIII-resistant hemophilia.

The present invention relates to an agent for the therapy of hemophilia A which is resistant to treatment with factor VIII, obtainable by maintaining a mixture of factor VIII, antithrombin III, a phospholipid and calcium ions in an aqueous solution at a temperature of from 1° to 45° C., preferably 37° C., for at least 1 minute, adding factor IX, and maintaining the solution at a temperature of from 1° to 45° C., preferably 20° C., until addition of a sample of this solution to an inhibitor plasma results in a partial thromboplastin time (PTT) of 15 to 30 seconds, where appropriate adding a polyol and, where appropriate, an amino acid, and, where appropriate, drying the solution.

The invention also relates to the process for preparing this agent.

An activation complex is produced during the incubation, via the interaction of the factors with phospholipids and Ca ions, and is able to activate the endogenous coagulation pathway even in the presence of isoantibodies against F VIII. A precondition for this is that the factors are present in the activation mixture in a particular ratio, preferably 0.5–2 U of F IX and 0.5–1 U of AT III, relative to 4 U of F VIII with at least 25 μg of phospholipid and a concentration of $CaCl_2$ corresponding to 0.75 mmol/l.

It was surprising that the process according to the invention results in an agent which has no amidolytic or proteolytic activity, as has been found by testing on the chromogenic substrates S-2238 and S-2222 supplied by Kabi, and which does not convert fibrinogen into fibrin either. Accordingly, this agent cannot contain any activated enzymes. This is consistent with its formation in the activation mixture in the presence of AT III, and the lack of adverse effects on its action by the latter, as is evident from the reduction in the partial thromboplastin time (PTT) which has been pathologically increased by inhibitors.

The agent prepared by this process remains stable for several days at 4° C. This is surprising, since it is known that activation complexes, as are formed in the body in the form of activators of factor X or prothrombin, are unstable.

It was also surprising that the agent obtained in this process loses effect when it is frozen in aqueous solution and thawed again or freeze-dried. However, the agent recovers its activity when it is heated after thawing, preferably at 30°–37° C. The reactivation corresponds to the activation shown in the figure. In view of the inactivation by freezing and freeze-drying, it was surprising that it was possible to prevent inactivation by addition of carbohydrates, preferably the disaccharide sucrose.

Finally, it was also surprising that the inhibitor-neutralizing activity of the agent according to the invention appeared in the exclusion peak after separation on Sepharose CL 6B. The fractions containing the activity were found also to contain all the phospholipids which had been added. Using the technique of immunoblotting (after separation by SDS polyacrylamide gel electrophoresis) it was possible to detect in these fractions derivatives of F VIII, F IX, AT III and a component which had a molecular weight of 100 kD and was not present in any of the factor concentrates which had been added. These findings suggest that the agent according to the invention is identical to a complex of modified F VIII and F IX which is formed under protection by AT III with phospholipids and Ca ions.

The examples which follow illustrate the invention.

Materials used for the preparation and characterization of the agent according to the invention in the examples which follow:

factor VIII: all commercially available factor VIII concentrates, including F VIII preparations, also of biotechnological origin, especially pasteurized products; preferably ®Haemate P, factor VIII concentrate of Behringwerke AG Marburg (Federal Republic of Germany) 50 IU/ml, dialyzed against sodium acetate buffer, 0.02 mol/l, pH 7.0, containing 0.06 mol/l NaCl and 1% glycine;

factor IX: factor IX concentrate HS Behringwerke, containing no heparin and containing no citrate ions owing to dialysis against the abovementioned sodium acetate buffer (120 IU/ml F IX);

phospholipid solution: a tetrahydrofuran extract from placentae which have been washed free of blood and dried, 250 mg of which have been emulsified in 50 ml of distilled water, sterilized by filtration and sonicated at 50,000 Hz for 20 min in an ice bath at 0° C., and then centrifuged at 100,000×g at 4° C. for 1 hour. The clear supernatant was used. It contains a mixture of the following phospholipids: phosphatidylethanolamine (PE), phosphatidylserine (PS), phosphatidylcholine (PC), phosphatidylinositol (PI), sphingomyelin (Sph) and lysophosphoglycerides (L);

0.1 mol/l aqueous calcium chloride solution;

antithrombin III solution: ®Kybernin HS 500 (Behringwerke AG). 1 pack containing 500 U, determined as heparin cofactor, dissolved in 10 ml of distilled water;

sucrose: extra pure (Merck, Darmstadt, Federal Republic of Germany);

buffers:
a) 20 mmol/l Na acetate, 20 mmol/l NaCl, pH 7.5 (conductivity 3.8 mS/cm, 25° C.)
b) 50 mmol/l imidazole, 20 mmol/l NaCl, pH 7.5 (conductivity 3.7 mS/cm, 25° C.).

EXAMPLE 1

1. Preparation of the agent according to the invention 1.4 ml of factor VIII concentrate were diluted with 14.5 ml of buffer a, and 175 µl of antithrombin III solution, 80 µl of phospholipid solution, 120 µl of calcium chloride solution and 0.32 g of sucrose were added, and the mixture was maintained at 37° C. for 30 minutes. Then 70 µl of factor IX solution were pipetted in. The mixture was maintained at 20° C. for 3 hours, and at defined time intervals (figure) aliquots were removed and tested by determination of the partial thromboplastin time (PTT) in an "inhibitor plasma", that is to say a plasma which contains antibodies against factor VIII. Mixtures which contained no phospholipid or no calcium chloride were used as controls. The test procedure was such that, at 37° C., 0.1 ml of the mixture prepared above, 0.1 ml of a PTT reagent, for example ®Pathromtin and, 6 min later, 0.1 ml of 0.025 mol/l calcium chloride solution were added to 0.1 ml of inhibitor plasma with 80 Bu/ml (Bu=Bethesda units).

The figure contains the results:
x agent according to the invention;
+ this agent without calcium ions;
o this agent without phospholipid.

2. Characterization of the agent according to the invention using hemophilia A plasmas containing inhibitors of F VIII:C The agent prepared under 1. was tested on inhibitor plasmas having various titers of antibodies.

The results are shown in the Table which follows.

TABLE 1

| Inhibitor titer | 80 Bu | 160 Bu | 320 Bu | 640 Bu |
|---|---|---|---|---|
| PTT (sec) | 29.3 | 30.5 | 31.3 | 35.8 |
| | 29.6 | 30.5 | 31.6 | 35.0 |

The results show that the pathologically increased PTT of inhibitor plasmas with antibody titers corresponding to 80–640 Bu/ml is normalized by the agent according to the invention. Both the inhibitor plasma with 80 and that with 640 Bu resulted without addition of an agent of this type in PTTs of about 120 seconds, and these could not be reduced on addition of factor VIII. Hence the experimental results in Table 1 show clearly that the agent according to the invention is not captured and neutralized by the inhibitors—in contrast to factor VIII. Thus this agent is very suitable for the therapy of hemophiliacs with inhibitors of factor VIII, for example of the isoantibody type.

The efficacy of the agent according to the invention can also be demonstrated by thromboelastography (TEG) with citrated whole human blood.

When citrated whole blood (230 µl) had been mixed with inhibitor plasma (20 µl containing 1,400 Bu/ml), as expected the r and k times of the thromboelastograms increased. The increased r and k values were normalized by addition of the agent according to the invention from Example 1 (10 µl).

3. Stability of the agent according to the invention in citrated plasma

In order to test the stability of the agent according to the invention in citrated human plasma, it was incubated in the ratio 1+1 or 1+7 with citrated human plasma. At defined times 0.2 ml aliquots were removed from the mixture and incubated with 0.1 ml of PTT reagent and, after 6 min at 37° C., 0.1 ml of 0.025 mol/l CaCl$_2$ solution was added. The PTTs obtained after defined incubation times are recorded in Table 2 which follows.

TABLE 2

Stability of the activator complex in citrated plasma at 37° C. (figures: PTT in seconds)

| | Control* | Incubation times in minutes | | | | |
|---|---|---|---|---|---|---|
| | | 0 | 7 | 15 | 60 | 150 |
| Agent + citrated plasma (1 + 1) | 41.6 | 21.6 | 24.4 | 25.2 | 26.0 | 29.5 |
| | 41.5 | 22.1 | 24.6 | 25.0 | 26.1 | 29.2 |
| Agent + citrated plasma (1 + 7) | 40.1 | 31.4 | 33.6 | 34.2 | 34.9 | |
| | 39.1 | 31.1 | 33.1 | 34.2 | 35.1 | |

*agent according to the invention replaced by buffer a.

It is evident from the results that the agent is stable for at least one hour in citrated plasma and, moreover, is still effective after 2½ hours. The reduction in the PTT from that with the buffer control shows that the agent has a potent procoagulant effect on citrated plasma. Since there is no loss of effect even during incubation with citrated plasma, the effect cannot be linked to a coagulation enzyme; this is because citrated plasma contains antithrombin III which neutralizes all coagulation enzymes.

EXAMPLE 2

To prepare the agent according to the invention, 80 ml of F VIII concentrate were mixed with 920 ml of buffer b; this resulted in 1,000 ml of F VIII solution which contained 4 U/ml and to which the following substances were admixed:
10.1 ml of AT III concentrate containing 50 U/ml,
5 ml of 0.5% strength (g/100 ml) phospholipid,
7.6 ml of 0.1 mol/l $CaCl_2$ solution and
20 g of sucrose.

This mixture was incubated at 37° C. for 30 min and then 4.2 ml of F IX concentrate (120 U of F IX/ml) were added, and the mixture was incubated at 20° C. for 3 h. During this time, the PTT in an inhibitor plasma measured therewith had decreased to 25 sec. The solution was sterilized by filtration, packed in 10 ml portions and freeze-dried. This lyophilisate was dissolved in the original volume, and an amount corresponding to 4 ml/kg of body weight was injected i.v. into rabbits. The placebo received by the animals was a solution which had been prepared in analogy to the above solution but contained no calcium chloride. Blood was taken after 5, 10, 15 and 30 min from the two animal groups, each comprising 3 rabbits, and the PTT in the plasma obtained therefrom was determined, once without addition and, on the other hand, with the addition of inhibitor plasma from a hemophilia A patient. The results have been tabulated, from which it can be seen that the PTT of the rabbits which received placebo was reduced slightly only after 5 min, but PTT of the animals which received injections of the agent according to the invention (Table 3 a) was decreased considerably more.

The plasma of the Latter group of animals also reduced the PTT which had been artificially increased by the addition of inhibitors (Table 3 b).

This demonstrates that the agent according to the invention circulates in active form in the animal.

TABLE 3 a

| PTT determination without addition of inhibitor plasma | | | | |
|---|---|---|---|---|
| | before | administration | | after |
| | | 5 min | 15 min | 30 min |
| Agent according to the invention (3 rabbits) | 41.7 | 34.7 | 37.9 | 42.2 |
| Placebo (3 rabbits) | 42.4 | 38.5 | 46.6 | 42.0 |

PTT determination:
0.1 ml of rabbit plasma
0.1 ml of diethylbarbiturate/acetate buffer, pH 7.6
0.1 ml of ® Pathromtin
120 sec, 37° C.
0.1 ml of 0.025 mol/l $CaCl_2$.

TABLE 3 b

| PTT determination with addition of inhibitor plasma | | | | |
|---|---|---|---|---|
| | before | administration | | after |
| | | 5 min | 15 min | 30 min |
| Agent according to the invention (3 rabbits) | 50.2 | 45.1 | 45.2 | 47.2 |
| Placebo (3 rabbits) | 61.0 | 60.2 | 61.5 | 61.0 |

PTT determination:
0.1 ml of rabbit plasma
0.1 ml of inhibitor plasma, 80 Bu/ml
0.1 ml of ® Pathromtin
360 sec, 37° C.
0.1 ml of 0.025 mol/l $CaCl_2$.

All the inhibitor-neutralizing activity was found in the exclusion volume when the agent according to the invention was subjected to separation on Sepharose CL 6B. The phospholipids were also identified in the same fractions, as were, on analysis of the samples using the immunoblotting technique with antisera against FVIII, FIX and antithrombin III, the following components: in addition to von Willebrand factor the modified L chain of FVIII:C as doublet with molecular weights of 70–75 kD, FIX, antithrombin III, and a component with a molecular weight of 100 kD.

We claim:

1. An agent for the therapy of Factor VIII inhibitor type hemophilia, said agent being stable in citrated human plasma and having no amidolytic or proteolytic activity, said agent comprising a composition obtained by maintaining a mixture of Factor VIII, antithrombin III, a phospholipid and calcium ions in an aqueous solution at a temperature of from 1° to 45° C. for at least one minute, adding Factor IX, and maintaining the solution at a temperature of from 1° to 45° C. until addition of a sample of this solution to an inhibitor plasma results in a partial thromboplastin time (PTT) of 15 to 30 seconds.

2. An agent as claimed in claim 1, wherein the mixture contains per 4 International Units of factor VIII activity, the following:
  a. 05.–2 International Units of factor IX activity,
  b. 0.5–1 International Units of antithrombin III activity,
  c. at least 25 μg of phospholipid; and
  d. 0.6–0.9 mmol/liter calcium ions.

3. The agent as claimed in claim 1 further containing a polyol.

4. The agent as claimed in claim 1, further containing an amino acid.

5. The agent as claimed in claim 1, which is in a dried form.

6. The therapeutic agent prepared as claimed in claim 1 that has potent procoagulant action while containing no activated coagulation enzymes as shown by testing on chromogenic substrates for factor IIa and Xa; is capable of reducing the partial thromboplastin time of normal citrated human plasma and of plasma containing inhibitors of factor VIII:C; said procoagulant action is not impaired by the presence of antibodies against factor IX; and upon gel filtration on Sepharose CL 6B, the activity of the agent migrates in the exclusion volume, and the fractions with inhibitor activity contain phospholipids, von Willebrand antigen, the modified light chain of factor VIII:C, factor IX, a component having a molecular weight of 100 kD, and antithrombin III.

* * * * *

UNITED STATES PATENT AND TRADEMARK OFFICE
CERTIFICATE OF CORRECTION

PATENT NO. : 5,091,363
DATED : February 25, 1992
INVENTOR(S) : Norbert Heimburger et al.

It is certified that error appears in the above-identified patent and that said Letters Patent is hereby corrected as shown below:

Abstract, line 7, change "offrom" to --of from--.

Claim 6, column 6, line 62, change "inhibitor" to --inhibitory--.

Signed and Sealed this

Fourteenth Day of September, 1993

Attest:

BRUCE LEHMAN

*Attesting Officer*    *Commissioner of Patents and Trademarks*